United States Patent
Wang et al.

(10) Patent No.: US 10,954,325 B2
(45) Date of Patent: Mar. 23, 2021

(54) RAFT AGENTS AND THEIR USE IN THE DEVELOPMENT OF POLYVINYLPYRROLIDONE GRAFTED NANOPARTICLES

(71) Applicant: UNIVERSITY OF SOUTH CAROLINA, Columbia, SC (US)

(72) Inventors: Lei Wang, Mount Pleasant, SC (US); Brian Benicewicz, Columbia, SC (US)

(73) Assignee: University of South Carolina, Columbia, SC (US)

(*) Notice: Subject to any disclaimer, the term of this patent is extended or adjusted under 35 U.S.C. 154(b) by 59 days.

(21) Appl. No.: 16/545,370

(22) Filed: Aug. 20, 2019

(65) Prior Publication Data
US 2020/0002447 A1 Jan. 2, 2020

Related U.S. Application Data

(62) Division of application No. 15/641,492, filed on Jul. 5, 2017, now Pat. No. 10,494,461, which is a division of application No. 14/805,531, filed on Jul. 22, 2015, now Pat. No. 9,732,169.

(60) Provisional application No. 62/027,510, filed on Jul. 22, 2014.

(51) Int. Cl.
| C08F 126/10 | (2006.01) |
| C07D 295/194 | (2006.01) |
| C07D 277/16 | (2006.01) |
| C08F 292/00 | (2006.01) |

(52) U.S. Cl.
CPC .......... *C08F 126/10* (2013.01); *C07D 277/16* (2013.01); *C07D 295/194* (2013.01); *C08F 292/00* (2013.01); *C08F 2438/03* (2013.01)

(58) Field of Classification Search
CPC ... C08F 126/10; C08F 292/00; C08F 2438/03
See application file for complete search history.

(56) References Cited

U.S. PATENT DOCUMENTS

| 3,646,094 | A | 2/1972 | Brooks et al. |
| 6,153,705 | A | 11/2000 | Corpart et al. |
| 6,458,968 | B2 | 10/2002 | Benicewicz et al. |
| 7,332,552 | B2 | 2/2008 | Benicewicz et al. |
| 8,865,796 | B2 | 10/2014 | Benicewicz et al. |
| 9,187,643 | B2 | 11/2015 | Benicewicz et al. |
| 9,249,250 | B2 | 2/2016 | Benicewicz et al. |

(Continued)

OTHER PUBLICATIONS

Wang, Journal of Magnetism and Magnetic Materials, 340, (2013) p. 57-60 (Year: 2013).*

(Continued)

*Primary Examiner* — Robert C Boyle
(74) *Attorney, Agent, or Firm* — Dority & Manning, P.A.

(57) ABSTRACT

Nanoparticles having a plurality of PVP chains covalently bonded to a surface of the nanoparticle are provided, along with their methods of formation and the RAFT agents for the polymerization of the PVP chains. RAFT agents are generally provided, along with their methods of formation and use. Methods are also generally provided for grafting a PVP polymer onto a nanoparticle. In one embodiment, the method includes polymerizing a plurality of monomers in the presence of a RAFT agent to form a polymeric chain covalently bonded to the nanoparticle.

8 Claims, 9 Drawing Sheets

(56) References Cited

U.S. PATENT DOCUMENTS

| | | | |
|---|---|---|---|
| 9,359,453 B2 | 6/2016 | Benicewicz et al. | |
| 9,475,922 B2 | 10/2016 | Benicewicz et al. | |
| 2003/0199653 A1* | 10/2003 | McCormick, III | C08F 2/44 526/219.6 |
| 2004/0118492 A1 | 7/2004 | Kim et al. | |
| 2006/0223936 A1 | 10/2006 | Such et al. | |
| 2007/0088140 A1 | 4/2007 | Benicewicz et al. | |
| 2008/0139764 A1 | 6/2008 | Le et al. | |
| 2010/0241071 A1* | 9/2010 | Atanasoska | A61L 27/446 604/103.02 |
| 2010/0261808 A1* | 10/2010 | Schadler | C08L 51/10 523/205 |
| 2013/0041112 A1* | 2/2013 | Benicewicz | C08K 9/04 525/342 |
| 2015/0343387 A1* | 12/2015 | Kim | B01D 71/42 210/500.25 |

OTHER PUBLICATIONS

Arsalani, eXPRESS Polymer Letters, vol. 4, In No. 6 (2010) p. 329-338 (Year: 2010).*

Bhattacharjee, et al. "Protein-Polymer Grafts via a Soy Protein Derived Macro-RAFT Chain Transfer Agent" *J. Polym. Environ.* 19 (2011) pp. 203-208.

Chapman, et al. "Multi-shell Soft Nanotubes from Cyclic Peptide Templates" *Adv. Mater.* 25 (2013) pp. 1170-1172.

Chiefari, et al. "Living Free-Radical Polymerization by Reversible Addition-Fragmentation Chain Transfer: The RAFT Process" *Macromolecules* 31 (1998) pp. 5559-5562.

Kanagasabapathy, et al. "Montmorillonite K 10-catalyzed regioselective addition of thiols and thiobenzoic acids onto olefins: an efficient synthesis of dithiocarboxlyic esters" *Tetrahedron Letters* 42 (2001) pp. 3791-3794.

Mayadunne, et al. "Living Radical Polymerization with Reversible Addition Fragmentation Chain Transfer (RAFT Polymerization) Using Dithiocarbamates as Chain Transfer Agents" *Macromolecules* 32 (1999) pp. 6977-6980.

Rieger, et al. "Surfactant-Free RAFT Emulsion Polymerization using Poly(N,N-dimethylacrylamide) Trithiocarbonate Macromolecular Chain Transfer Agents" *Macromolecules* 43 (2010) pp. 6302-6310.

Sudalai, et al. "Phosphorus Pentasulfied: A Mild and Versatile Catalyst/Reagent for the Preparation of Dithiocarboxylic Esters" *Organic Letters* 2(20) (2000) pp. 3213-3216.

Thang, et al. "A Novel Synthesis of Functional Dithioesters, Dithiocarbamates, Xanthates and Trithiocarbonates" *Tetrahedron Letters* 40 (1999) pp. 2435-2438.

Zhang, et al. "Synthesis and Investigation of Well-Defined and Fluorescence-Labelled Poly(methyl methacrylate) by RAFT Polymerization" *Acta Polymerica Sinica* 6 (2010) p. 691-698.

* cited by examiner

RAFT AGENTS AND THEIR USE IN THE DEVELOPMENT OF POLYVINYLPYRROLIDONE GRAFTED NANOPARTICLES

PRIORITY INFORMATION

The present application claims priority to and is a divisional application of U.S. patent application Ser. No. 15/641,492, filed on Jul. 5, 2017, which claims priority to and is a divisional application of U.S. patent application Ser. No. 14/805,531, filed on Jul. 22, 2015, now U.S. Pat. No. 9,732,169, which claims priority to U.S. Provisional Patent Application Ser. No. 62/027,510, titled "Novel RAFT Agents and Their Use in the Development of Polyvinylpyrrolidone Grafted Nanoparticles," of Benicewicz, et al., filed on Jul. 22, 2014, the disclosures of which are incorporated by reference herein.

BACKGROUND

Polymer grafted nanoparticles are very appealing composite materials ascribed to their broad applications in coatings, biomedical field and chemosensors. In addition, the properties of the composites can be tailored by choosing different substrate nanoparticles and polymer shells. The graft density and chain lengths of the surface attached polymers are able to greatly affect the dispersion and the final properties of the nanoparticles. Thus, controlling the growth of polymer on surfaces is extremely significant.

Poly(vinyl pyrrolidone) (PVP), a very important water soluble polymer, has been widely applied in biomedical area and cosmetic industry due to its nontoxic and nonionic characteristics, and its biocompatibility. It is particularly attractive in the drug delivery field ascribed to its abilities to conjugate active biomolecules and prolong the circulation lifetime of antibiotics in blood. Although PVP has been widely synthesized via free radical polymerization of N-vinyl pyrrolidone (NVP), the preparation of PVP grafted nanoparticles with great control on polymer chain length and architecture is desirable and extremely important for biomedical applications. Nitroxide Mediated Polymerization (NMP), atom transfer radical polymerization (ATRP), and organocobalt-mediated radical polymerization (OMRP) have demonstrated no effect or very little effect after careful design and operation, on the mediating polymerization of NVP in a controlled manner. The reason is the special polar lactam structure in the monomer, which interacts with the catalysts and further interrupts them in these polymerization systems.

Reversible addition-fragmentation chain transfer/macromolecular design by interchange of xanthates (RAFT/MADIX) polymerization has been widely used to synthesize polymers in a controlled manner (both molecular weight and polydispersity) since it does not require the use of inorganic catalysts and is adaptable to an extremely wide range of functional monomers. So far, O-ethyl xanthate-based RAFT/MADIX agents have been used in mediating the NVP polymerization. However, it was reported that the terminal O-ethyl xanthate on PVP chains is unstable and decomposed in polymerization. In addition, the terminal O-ethyl xanthate on PVP chains is hydrolyzed to form a hydroxyl end group after 16 h in a 40° C. aqueous environment. Thus, more thermally stable RAFT/MADIX agents are desirable for mediating the polymerization of NVP.

Dithiocarbamates have been used as a thermally stable agent in RAFT polymerization. So far, only a few groups have reported using dithiocarbamates to mediate the polymerization of NVP. However, these dithiocarbamate RAFT agents contained either bulky Z groups or alkyne based primary R groups, which are not good leaving groups and interfere with the polymerization due to the alkyne moiety. Thus, new dithiocarbamate RAFT agents are needed to mediate the polymerization of NVP.

Only a few groups have reported placing PVP on nanoparticles. In these reported PVP covered particles, PVP chains are physically absorbed on the particles' surfaces or grafted on surfaces without control (by free radical polymerizations). That is, PVP chains are physically absorbed on the particles' surfaces, rather than growing covalently attached chains from particle surfaces in a controlled manner.

Thus, a need exists for mediating the polymerization of NVP on nanoparticles in a controlled manner via surface-initiated RAFT polymerization.

SUMMARY

Objects and advantages of the invention will be set forth in part in the following description, or may be obvious from the description, or may be learned through practice of the invention.

RAFT agents are generally provided, along with their methods of formation and use. In one embodiment, a RAFT agent is provided that has the formula:

where $R_1$ is H or a $C_1$ to $C_5$ alkyl group; $R_2$ is an electron withdrawing group; $R_3$ is a hydroxyl group, a thioazoline group, or an ether group; and n is 1 to 12.

In another embodiment, a RAFT agent is provided that has the formula:

where $R_1$ is H or a $C_1$ to $C_5$ alkyl group; $R_2$ is an electron withdrawing group; $R_3$ is a hydroxyl group, a thioazoline group, or an ether group; and n is 1 to 12.

Methods are also generally provided for grafting a PVP polymer onto a nanoparticle. In one embodiment, the method includes: polymerizing a plurality of monomers in the presence of a RAFT agent to form a polymeric chain covalently bonded to the nanoparticle, wherein the plurality of monomers comprises N-vinylpyrrolidone, and wherein the RAFT agent is selected from the group consisting of:

where $R_1$ is H or a $C_1$ to $C_5$ alkyl group; $R_2$ is an electron withdrawing group; $R_3$ is a hydroxyl group, a thioazoline group, or an ether group; and n is 1 to 12; and where $R_1$ is H or a $C_1$ to $C_5$ alkyl group; $R_2$ is an electron withdrawing group; $R_3$ is a hydroxyl group, a thioazoline group, or an ether group; and n is 1 to 12.

Nanoparticles are also provided that can be formed from the method of grafting a PVP polymer onto a nanoparticle. In one embodiment, the nanoparticle includes a plurality of PVP chains covalently bonded to a surface of the nanoparticle.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

DEFINITIONS

Chemical elements are discussed in the present disclosure using their common chemical abbreviation, such as commonly found on a periodic table of elements. For example, hydrogen is represented by its common chemical abbreviation H; helium is represented by its common chemical abbreviation He; and so forth.

As used herein, the prefix "nano" refers to the nanometer scale (e.g., from about 1 nm to about 100 nm). For example, particles having an average diameter on the nanometer scale (e.g., from about 1 nm to about 100 nm) are referred to as "nanoparticles." Particles having an average diameter of greater than 1,000 nm (i.e., 1 μm) are generally referred to as "microparticles," since the micrometer scale generally involves those materials having an average size of greater than 1 μm.

As used herein, the term "polymer" generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

The term "organic" is used herein to refer to a class of chemical compounds that are comprised of carbon atoms. For example, an "organic polymer" is a polymer that includes carbon atoms in the polymer backbone, but may also include other atoms either in the polymer backbone and/or in side chains extending from the polymer backbone (e.g., oxygen, nitrogen, sulfur, etc.).

The "number average molecular weight" ($M_n$) is readily calculated by one of ordinary skill in the art, and generally refers to the ordinary arithmetic mean or average of the molecular weights of the individual macromolecules. It is determined by measuring the molecular weight of n polymer molecules, summing the weights, and dividing by n, such as represented in the formula:

$$\overline{M}_n = \frac{\sum_i N_i M_i}{\sum_i N_i}$$

where $N_i$ is the number of molecules of molecular weight $M_i$. The number average molecular weight of a polymer can be determined by gel permeation chromatography, and all colligative methods, like vapor pressure osmometry or end-group determination.

The "weight average molecular weight" ($M_w$) is readily calculated by one of ordinary skill in the art, and generally refers to:

$$\tilde{M}_w = \frac{\sum_i N_i M_i^2}{\sum_i N_i M_i}$$

where $N_i$ is the number of molecules of molecular weight $M_i$. The weight average molecular weight can be determined by light scattering, small angle neutron scattering (SANS), X-ray scattering, gel permeation chromatography, and sedimentation velocity.

The polydispersity index (PDI) is a measure of the distribution of molecular mass in a given polymer sample. The PDI calculated is the weight average molecular weight divided by the number average molecular weight. It indicates the distribution of individual molecular masses in a batch of polymers. The PDI has a value equal to or greater than 1, but as the polymer chains approach uniform chain length, the PDI approaches unity (i.e., 1).

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Novel RAFT agents are generally provided, along with their methods of formation and use. For example, the RAFT agents can be utilized as a RAFT agent for free radical polymerization of N-vinyl pyrrolidone (NVP) to form grafted poly(vinyl pyrrolidone) on nanoparticles with control of polymer chain length and polydispersity.

I. RAFT Agents

Reversible Addition-Fragmentation chain Transfer polymerization (RAFT) is one type of controlled radical polymerization. RAFT polymerization uses thiocarbonylthio compounds, such as dithioesters, dithiocarbamates, trithiocarbonates, and xanthates, in order to mediate the polymerization via a reversible chain-transfer process. RAFT polymerization can be performed by simply adding a chosen quantity of appropriate RAFT agents (thiocarbonylthio compounds) to a conventional free radical polymerization. RAFT polymerization is particularly useful with monomers having a vinyl functional group (e.g., a (meth)acrylate group).

Typically, a RAFT polymerization system includes the monomer, an initiator, and a RAFT agent (also referred to as a chain transfer agent). Because of the low concentration of the RAFT agent in the system, the concentration of the initiator is usually lower than in conventional radical polymerization. Suitable radical initiators can be azobisisobutyronitrile (AIBN), 4,4'-azobis(4-cyanovaleric acid) (ACVA), etc.

RAFT agents are generally thiocarbonylthio compounds, such as generally shown in the generic formula below:

Formula of a generic RAFT agent where the Z group primarily stabilizes radical species added to the C═S bond and the R' group is a good homolytic leaving group which is able to initiate monomers. For example, the Z group can be an alkyl group; an aryl group (e.g., phenyl group, benzyl group, etc.); a thiol group (e.g., R—S—, with R being H or any suitable organic group, such as alkyl, aryl, etc.); an amine group (e.g., $R_2N$—, with each R group being independently H or any suitable organic group, such as alkyl, aryl, etc.); or an oxy group (R—O—, with R being any suitable organic group, such as alkyl, aryl, etc.), etc. The R' group can be an organic chain terminating with a carboxylic acid group, a carboxylic derivative, an alkyne group, an azide group, an alcohol group, an alkene group, or another group that is reactive with the functional group of the particular anchoring compound attached to the nanoparticle. That is, in one particular embodiment, the functional group of the anchoring compound present on the nanoparticle is reactive with the R' group of the RAFT agent to ensure sufficient covalent bonding there between.

As stated, RAFT is a type of living polymerization involving a conventional radical polymerization in the presence of a reversible chain transfer reagent. Like other living radical polymerizations, there is minimized termination step in the RAFT process. The reaction is started by radical initiators (e.g., AIBN). In this initiation step, the initiator reacts with a monomer unit to create a radical species which starts an active polymerizing chain. Then, the active chain reacts with the thiocarbonylthio compound, which kicks out the homolytic leaving group (R'). This is a reversible step, with an intermediate species capable of losing either the leaving group (R') or the active species. The leaving group radical then reacts with another monomer species, starting another active polymer chain. This active chain is then able to go through the addition-fragmentation or equilibration steps. The equilibration keeps the majority of the active propagating species into the dormant thiocarbonyl compound, limiting the possibility of chain termination. Thus, active polymer chains are in equilibrium between the active and dormant species. While one polymer chain is in the dormant stage (bound to the thiocarbonyl compound), the other is active in polymerization.

By controlling the concentration of initiator and thiocarbonylthio compound and/or the ratio of monomer to thiocarbonylthio compound, the molecular weight of the polymeric chains can be controlled with low polydispersities.

Depending on the target molecular weight of final polymers, the monomer to RAFT agent atomic ratios can range from about less than about 10 to more than about 10000 (e.g., about 10 to about 1,500). Other reaction parameters can be varied to control the molecular weight of the final polymers, such as solvent selection, reaction temperature, and reaction time. For instance, solvents can include conventional organic solvents such as tetrahydrofuran, toluene, dimethylformamide, anisole, acetonitrile, dichloromethane, etc., or mixtures of solvents. The reaction temperature can range from room temperature (e.g., about 20° C.) to about 120° C. The reaction time can be from less than about 1 hour to about 48 hours.

The RAFT process allows the synthesis of polymers with specific macromolecular architectures, such as block, gradient, statistical, comb/brush, star, hyperbranched, and network copolymers.

Because RAFT polymerization is a form of living radical polymerization, it is ideal for synthesis of block copolymers. For example, in the copolymerization of two monomers (A and B) allowing A to polymerize via RAFT will exhaust the monomer in solution with significantly suppressed termination. After monomer A is fully reacted, the addition of monomer B will result in a block copolymer. One requirement for maintaining a narrow polydispersity in this type of copolymer is to have a chain transfer agent with a high transfer constant to the subsequent monomer (monomer B in the example).

Due to the special polar lactam structure in the NVP monomer, new RAFT agents were developed for the formation of PVP polymers grafted onto nanoparticles. In one embodiment, a pyrrole-containing RAFT agent is provided having the structure of Formula 1a:

where $R_1$ is H or a $C_1$ to $C_5$ alkyl group (e.g., a methyl group, an ethyl group, a propyl group, a benzyl group, or a pentyl group); $R_2$ is a nitrile group (i.e., —CN) or another electron withdrawing group (e.g., —$NO_2$; —$SO_3H$; a halogen group such as —F, —Cl, —Br, —I; —S(=O)$_2$—R; —C(=O)—R; etc., with R being a generic organic group); $R_3$ is a hydroxyl group (—OH), a thioazoline group, or an ether group (e.g., —$OR_4$, with $R_4$ being a $C_1$ to $C_5$ alkyl group); and n is 1 to 12 (e.g., 2 to 10, such as 2 to 6).

In one embodiment, when $R_1$ is H; $R_2$ is CN; $R_3$ is a hydroxyl group; and n is 2, the resulting compound is 4-cyanopentanoic acid N-pyrroledithiocarboxylate (CPDC) as shown in Formula 2a:

The RAFT agent of Formula 2a can be activated through reaction with 2-mercaptothiazoline to form activated CPDC (i.e., CPDC having its carboxylic acid functional group replaced with a 2-mercaptothiazoline-containing functional group). In such an embodiment, the RAFT agent can be described as when $R_1$ is H; $R_2$ is CN; $R_3$ is a thioazoline group; and n is 2, the resulting compound is an activated CPDC as shown in Formula 3a:

Although shown above with a pyrrole ring in Formula 1a, 1b, and 1c, any suitable nitrogen containing heterocyclic aromatic organic compound can be utilized in compound. For example, a pyridine ring can be utilized in place of the pyrrole ring, such as shown in the compound of Formula 1b:

where $R_1$ is H or a $C_1$ to $C_5$ alkyl group (e.g., a methyl group, an ethyl group, a propyl group, a benzyl group, or a pentyl group); $R_2$ is a nitrile group (i.e., —CN) or another electron withdrawing group (e.g., —$NO_2$; —$SO_3H$; a halogen group such as —F, —Cl, —Br, —I; —S(=O)$_2$—R; —C(=O)—R; etc., with R being a generic organic group); $R_3$ is a hydroxyl group (—OH), a thioazoline group, or an ether group (e.g., —$OR_4$, with $R_4$ being a $C_1$ to $C_5$ alkyl group); and n is 1 to 12 (e.g., 2 to 10, such as 2 to 6).

In one embodiment, when $R_1$ is H; $R_2$ is CN; $R_3$ is a hydroxyl group; and n is 2, the resulting compound is 4-cyanopentanoic acid N-pyridinedithiocarboxylate as shown in Formula 2b:

The RAFT agent of Formula 2b can be activated through reaction with 2-mercaptothiazoline to form activated CPDC (i.e., CPDC having its carboxylic acid functional group replaced with a 2-mercaptothiazoline-containing functional group). In such an embodiment, the RAFT agent can be described as when $R_1$ is H; $R_2$ is CN; $R_3$ is a thioazoline group; and n is 2, the resulting compound is a pyridine-containing RAFT Agent as shown in Formula 3b:

In any of the above given formulas, the nitrogen containing heterocyclic aromatic organic groups can be substituted with any suitable organic group (generically, an R group) at any position(s). For example, an alkyl group, alkyne group, an aromatic cyclic group (e.g., a pentene ring, a benzene ring, etc.) to form a polycyclic aromatic hydrocarbon group, a thio group, an amine group, an oxygen moiety, or the like (or combinations thereof), can be present on the nitrogen containing heterocyclic aromatic organic group.

II. Formation of RAFT Agents

Figure 1:
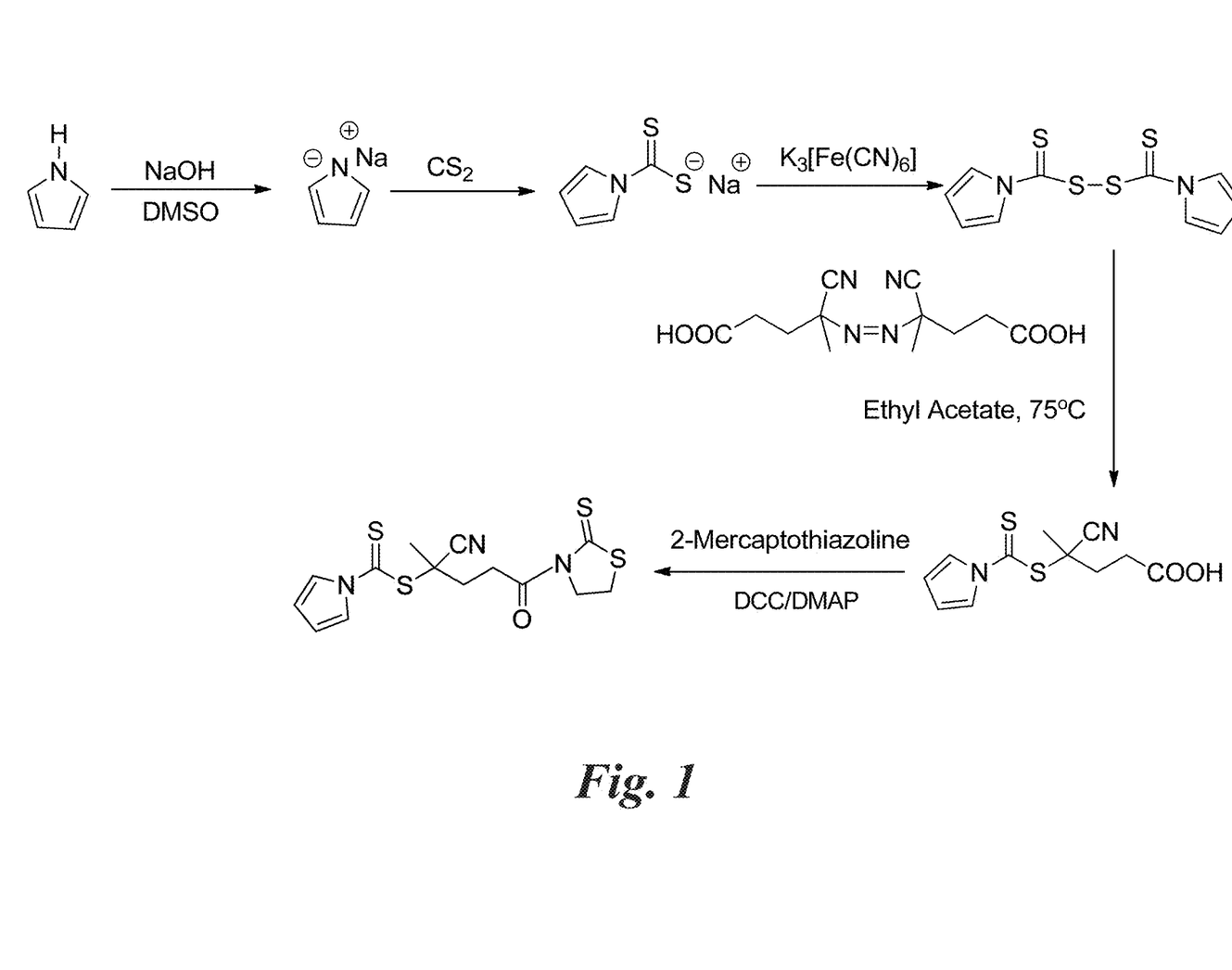
FIG. 1 shows an exemplary reaction scheme for the synthesis of CPDC.

FIG. 1 shows an exemplary method of formation of the RAFT agent of Formula 2a. As shown, a pyrrole anion is formed and then reacted with carbon disulfide ($CS_2$) to form a N-pyrroledithiocarboxylate anion. Then, two N-pyrroledithiocarboxylate anions can be reacted together to join with a di-sulfur bond, resulting in 1H-pyrrole-1-carbothioic dithioperoxyanhydride. Upon reaction with 4,4'-azobis(4-cyanopentanoic acid), the RAFT agent of Formula 2a is formed (i.e., CPDC). Then, the CPDC RAFT agent of Formula 2a can be activated through reaction with 2-mercaptothiazoline to form activated CPDC (i.e., CPDC having its carboxylic acid functional group replaced with a 2-mercaptothiazoline-containing functional group).

III. Use of RAFT Agents to Graft PVP Onto Nanoparticles

To form the grafted nanoparticles, the RAFT agents described above can be utilized in free radical polymerization of NPA to form PVP chains grafted to the surface of the nanoparticle (either directly or indirectly).

Two methods can be utilized to form the PVP chains extending from the nanoparticles via the anchoring compounds: a "grafting-from" approach and a "grafting-to" approach. These strategies will be explained in more details in the following sections.

In one embodiment, monomers can be polymerized through this method including but not limited to NVP, the structure of which is shown in Formula 4:

Such a NVP monomer can be utilized to form a PVP polymeric chain grafted to the nanoparticles.

A. Nanoparticles

The presently disclosed methods can be utilized on a variety of different types of nanoparticles. The nanoparticle may comprise, for example, natural or synthetic nanoclays (including those made from amorphous or structured clays), inorganic metal oxides (e.g., silica, alumina, and the like), nanolatexes, organic nanoparticles, etc. Particularly suitable nanoparticles include inorganic nanoparticles, such as silica, alumina, titania ($TiO_2$), indium tin oxide (ITO), CdSe, etc., or mixtures thereof. Additionally, suitable nanoparticles can include metallic nanoparticles (e.g., Ti, gold, silver, etc.), polymer nanoparticles, carbon, graphite, graphene, carbon nanotubes, virus nanoparticles, polymer gel nanoparticles (e.g., alginate, or the like), etc., or mixtures thereof.

Nanoparticles, as used herein, includes particles (including, but not limited to, rod-shaped particles, disc-shaped particles, platelet-shaped particles, tetrahedral-shaped particles), fibers, nanotubes, or any other materials having at least one dimension on the nano scale. In one embodiment, the nanoparticles have an average particle size of about 1 nanometer to about 1000 nanometers, preferably 2 nanometers to about 750 nanometers. That is, the nanoparticles have a dimension (e.g., an average diameter or length) of about 1 to 1000 nm. Nanotubes can include structures up to 1 centimeter long, alternatively with a particle size from about 2 to about 50 nanometers. Due to their size, nanoparticles have very high surface-to-volume ratios.

The nanoparticles may be crystalline or amorphous. A single type of nanoparticle may be used, or mixtures of different types of nanoparticles may be used. If a mixture of nanoparticles is used, they may be homogeneously or non-homogeneously distributed in the composite material or a system or composition containing the composite material. Non-limiting examples of suitable particle size distributions of nanoparticles are those within the range of about 2 nm to less than about 750 nm, alternatively from about 2 nm to less than about 200 nm, and alternatively from about 2 nm to less than about 150 nm.

It should also be understood that certain particle size distributions may be useful to provide certain benefits, and other ranges of particle size distributions may be useful to provide other benefits (for instance, color enhancement requires a different particle size range than the other properties). The average particle size of a batch of nanoparticles may differ from the particle size distribution of those nanoparticles. For example, a layered synthetic silicate can have an average particle size of about 25 nanometers while its particle size distribution can generally vary between about 10 nm to about 40 nm.

In one embodiment, the nanoparticles can be exfoliated from a starting material to form the nanoparticles. Such starting material may have an average size of up to about 50 microns (50,000 nanometers). In another embodiment, the nanoparticles can be grown to the desired average particle size.

B. Attachment of PVP to Nanoparticles

As stated above, PVP is attached onto the surface of nanoparticles to form grafted-nanoparticles through RAFT polymerization of NVP.

In certain embodiments, an anchoring compound can be attached to the surface of the nanoparticle for subsequent attachment of the polymeric chain (e.g., via a "grafting-from" or "grafting-to" approach, as described in greater detail below). The anchoring compound is covalently bonded to the surface of the nanoparticle, either directly or via a functionalization group.

The particular anchoring compound can be selected based upon the type of nanoparticle. Generally, the anchoring compound has a functional group for further reaction to the polymer chain.

Figure 2:
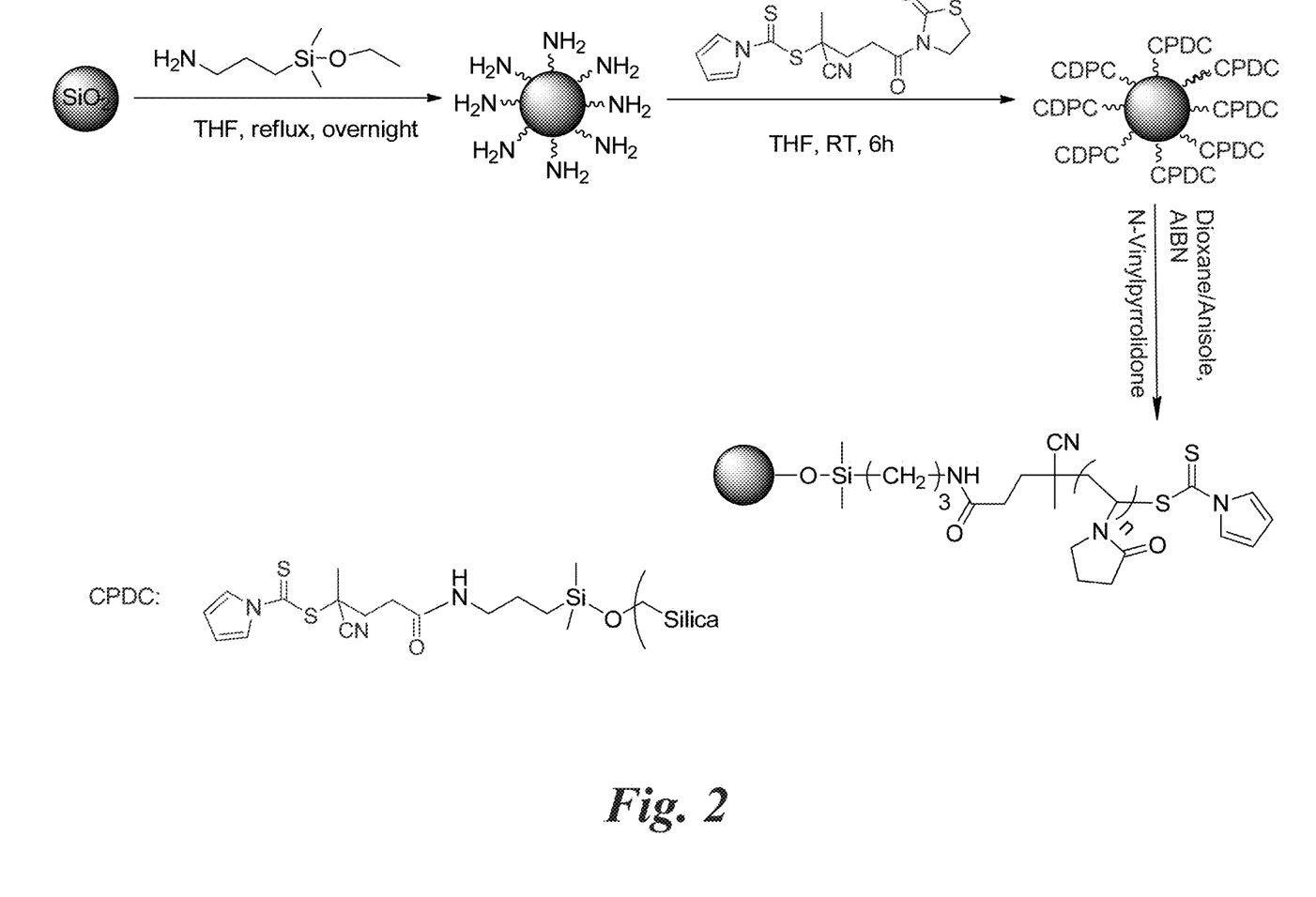
FIG. 2 shows an exemplary reaction scheme for the synthesis of PVP grafted silica nanoparticles.
Figure 3:
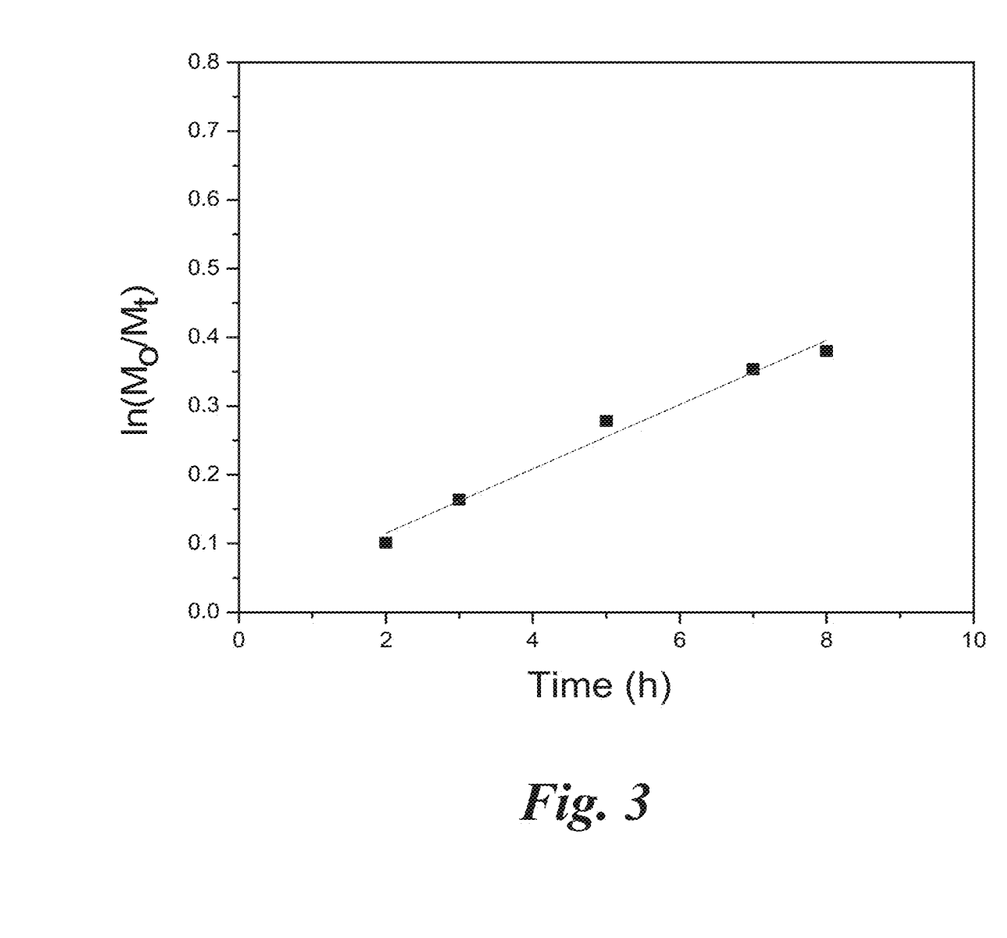
FIG. 3 shows a kinetic study for the CPDC mediated RAFT polymerization of NVP in dioxane/anisole (50%: 50%) ([NVP]:[CPDC]:[AIBN]=1000:1:0.2; monomer concentration: 6.83 mol/L) at 80° C., according to Example 1.
Figure 4:
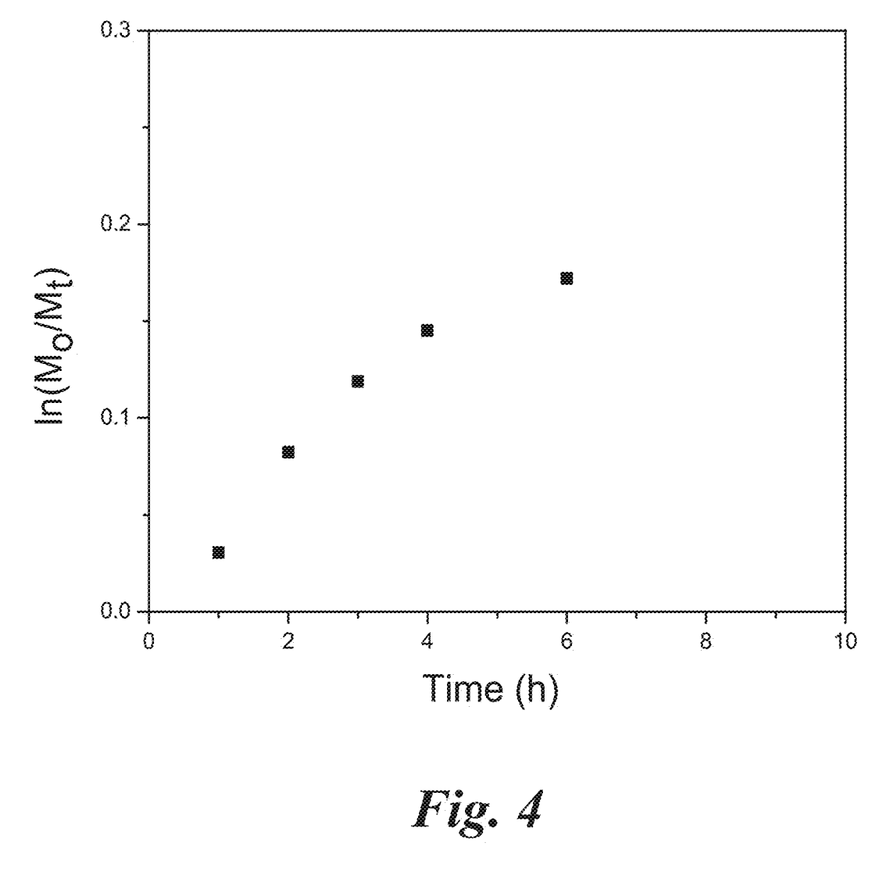
FIG. 4 shows a kinetic study for the RAFT polymerization of NVP mediated by CPDC coated silica nanoparticles in dioxane/anisole ([NVP]:[CPDC]:[AIBN]=1437:1:0.18; monomer concentration: 1.18 mol/L) at 80° C. according to Example 1.
Figure 5:
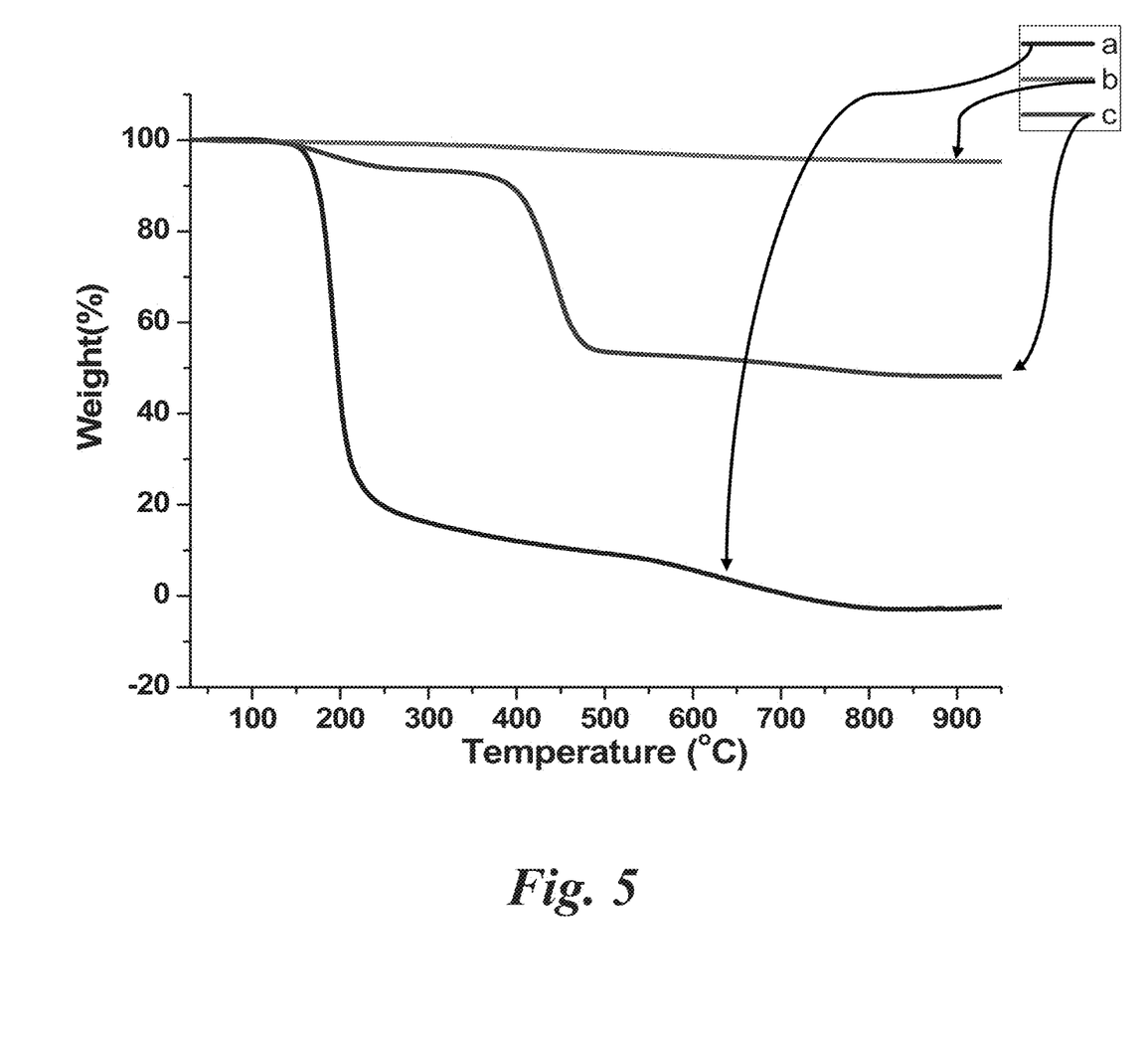
FIG. 5 shows the TGA of (a) CPDC; (b) CPDC coated nanoparticles; and (c) PVP grafted nanoparticles.
Figure 6A:
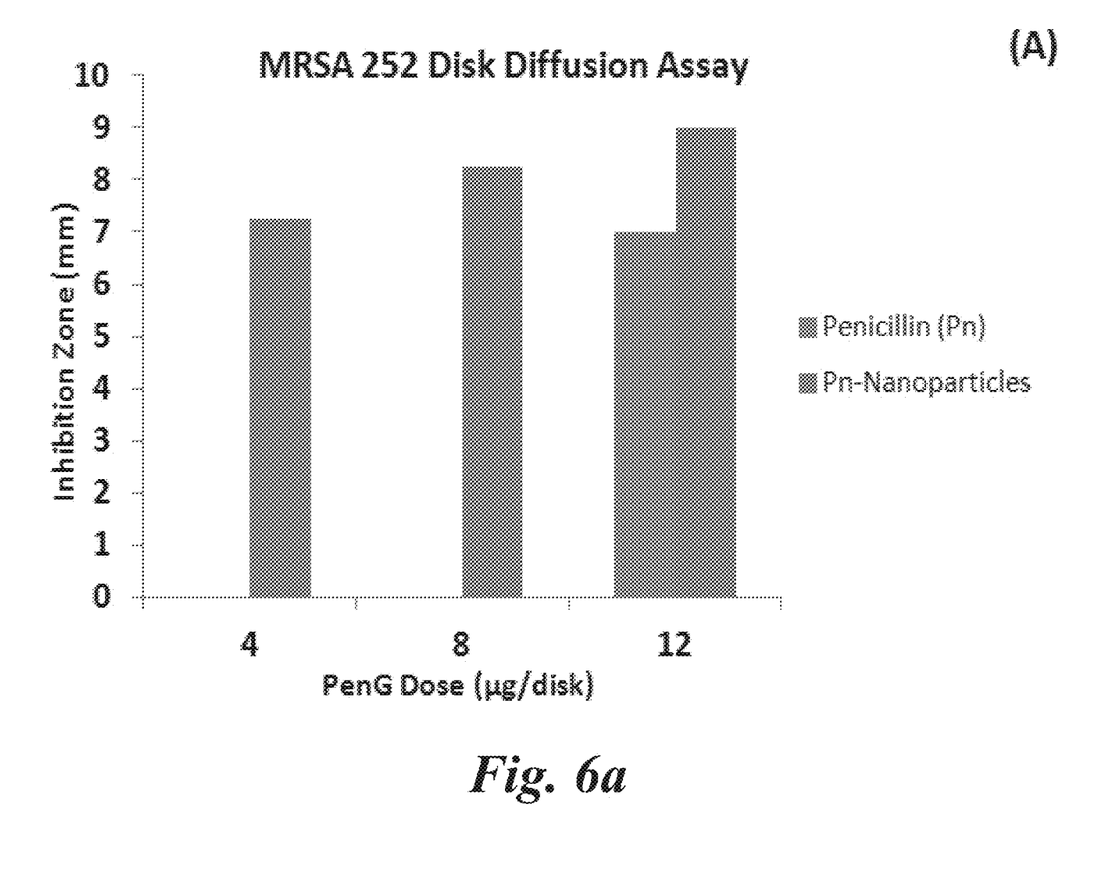
FIG. 6a shows the inhibition activity of free-PenG (left bar), PenG-Nanoparticles complex (right bar), as tested by disk-diffusion assays using MRSA 252, according to Example 2.
Figure 6B:
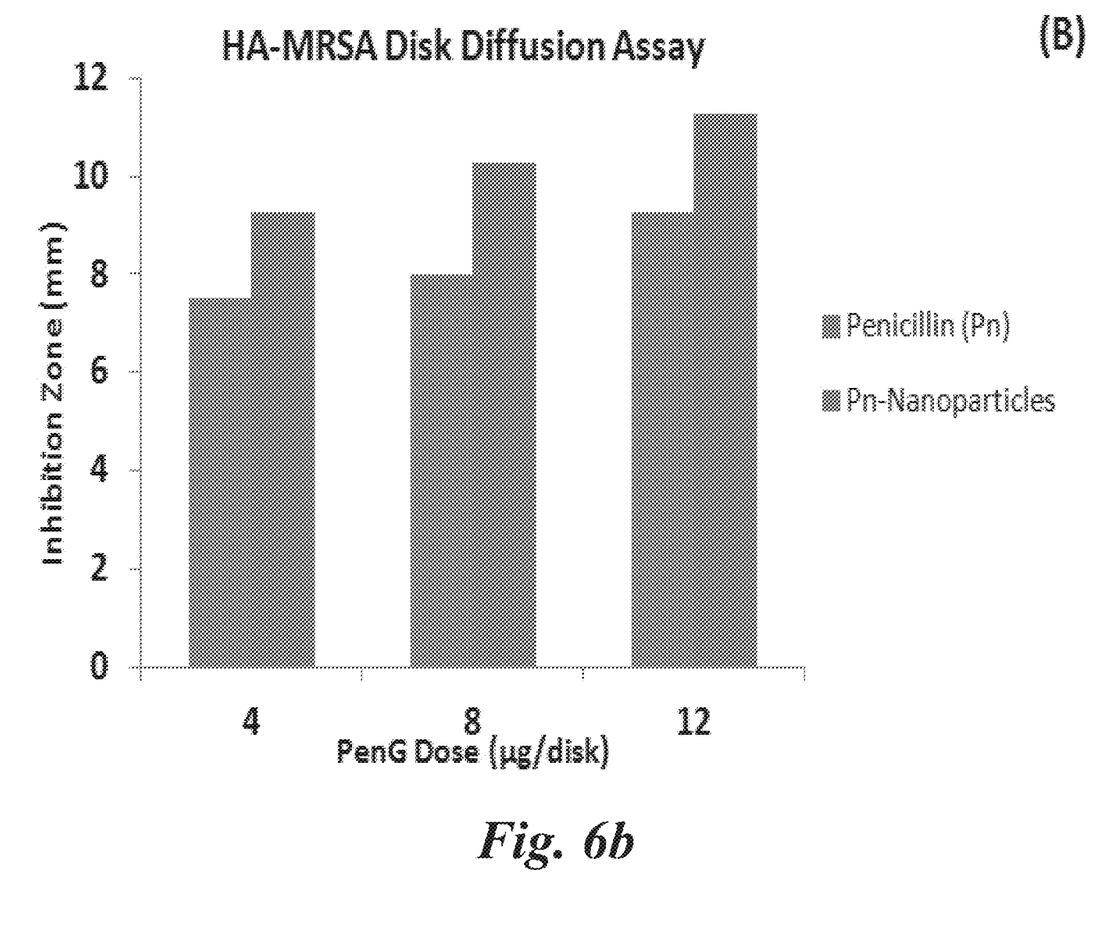
FIG. 6b shows the inhibition activity of free-PenG (left bar), PenG-Nanoparticles complex (right bar), as tested by disk-diffusion assays using HA-MRSA, according to Example 2.
Figure 6C:
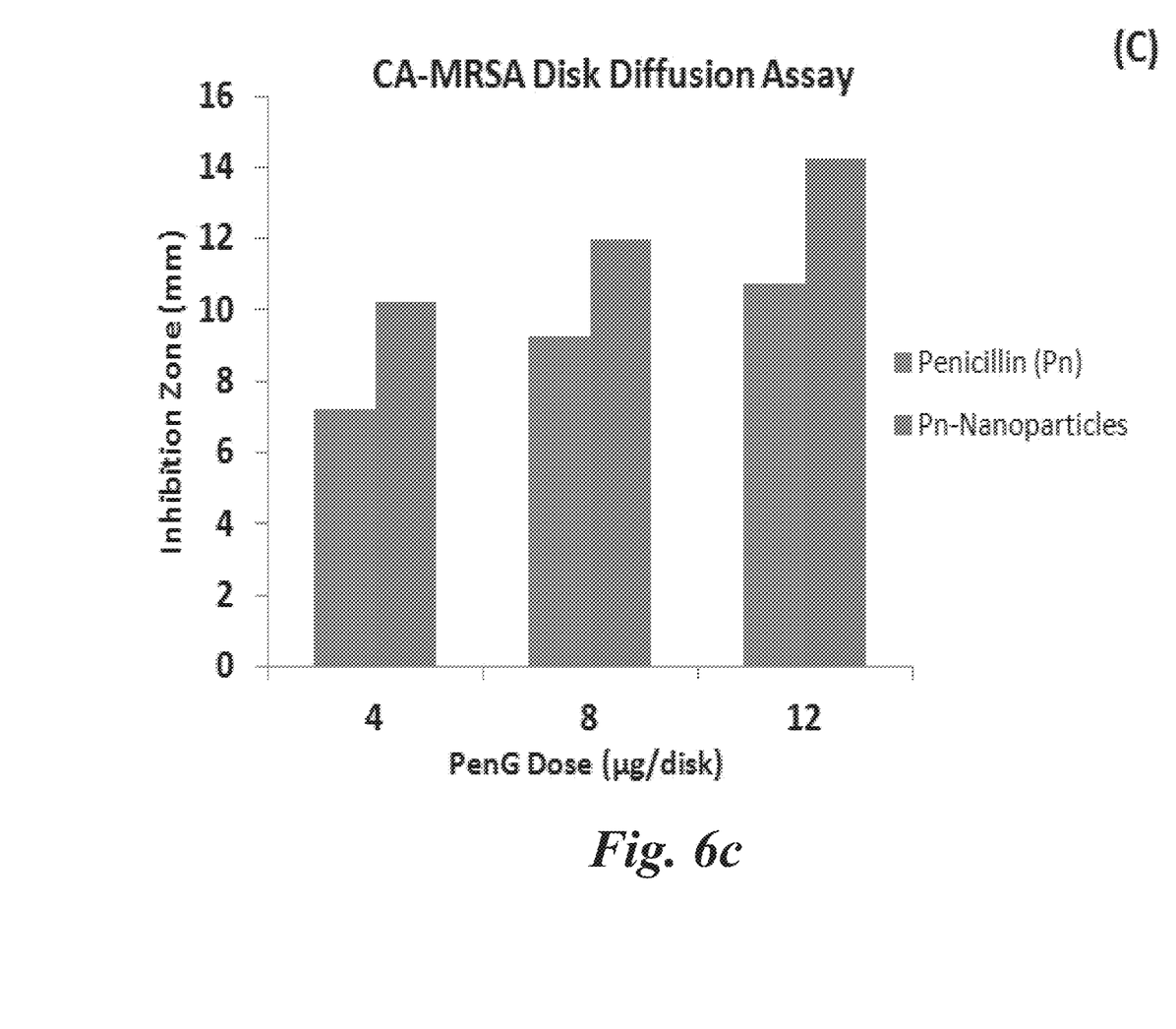
FIG. 6c shows the inhibition activity of free-PenG (left bar), PenG-Nanoparticles complex (right bar), as tested by disk-diffusion assays using CA-MRSA, according to Example 2.
Figure 6D:
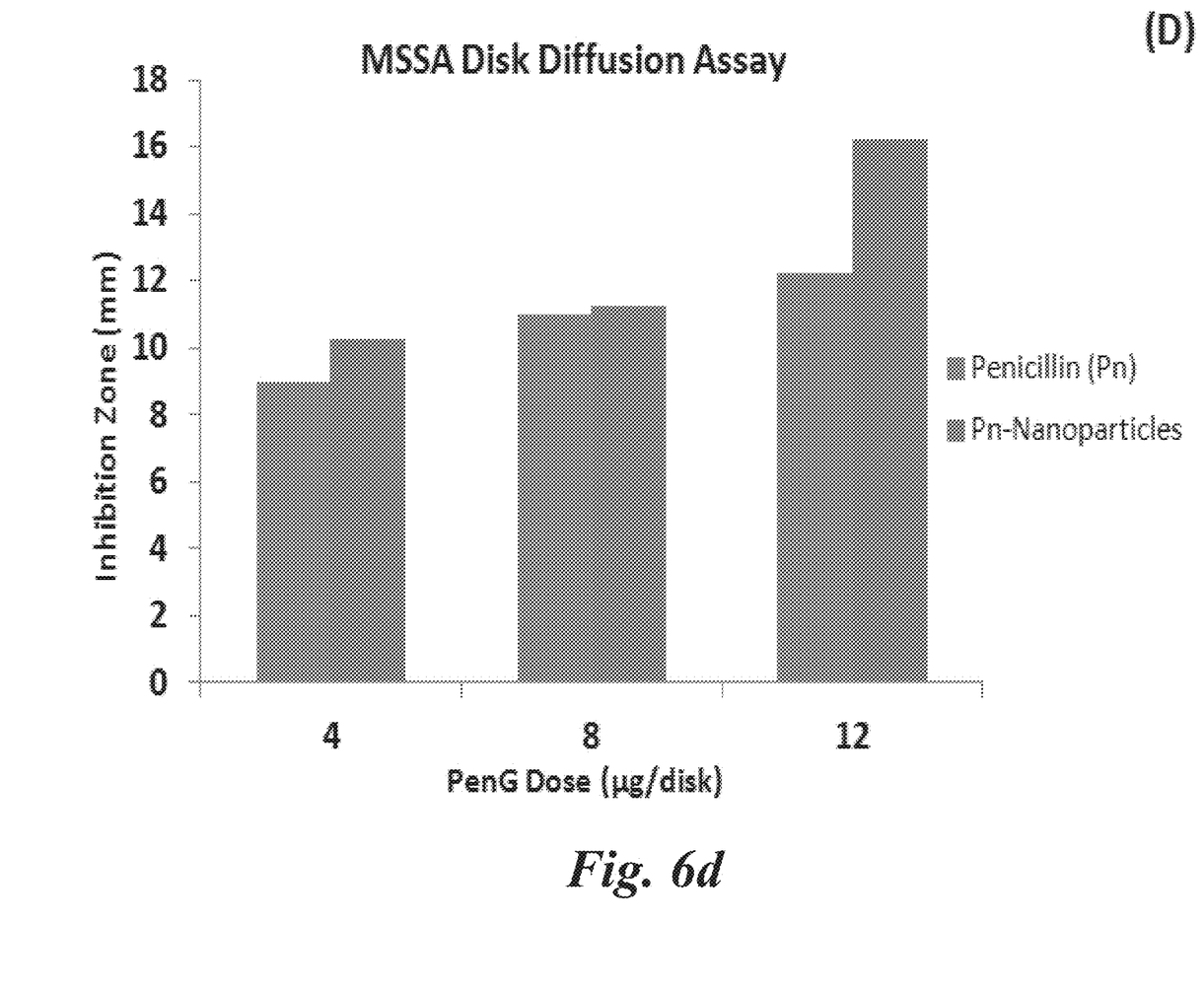
FIG. 6d shows the inhibition activity of free-PenG (left bar), PenG-Nanoparticles complex (right bar), as tested by disk-diffusion assays using MSSA, according to Example 2.

For example, referring to the first reaction step shown in FIG. 2, an anchoring compound having an amino-functionalization can be attached to the surface of a nanoparticle. In one embodiment, the amino-functionalization of the nanoparticles (i.e., attachment of amine groups to the nanoparticles) can be achieved through reaction of the nanoparticles with a mono-functional silane anchoring compound (e.g., 3-aminopropyldimethylmethoxysilane or 3-aminopropyldimethylethoxysilane). Use of a mono-functional silane as the anchoring compound, such as 3-aminopropyldimethylmethoxysilane or 3-aminopropyldimethylethoxysilane, compared to a difunctional or trifunctional silanes ensures the formation of a monolayer of anchoring agent on the silica surface and helps to prevent particle agglomeration by crosslinking during processing. However, mono-functional, di-functional, and tri-functional silanes are all suitable for use as an anchoring compound in the presently disclosed methods.

No matter the particular silane (i.e., mono-functional, di-functional, or tri-functional, etc.), the ratio of the silane to the nanoparticles is critical in determining the grafting density. In addition to adjusting the ratio by varying the concentration of the mono-functional silane, addition of a small amount of an inert dimethylmethoxy-n-octylsilane (or other alkoxy-alkyl silanes) can help to partially cover the nanoparticle surface by inert alkyl groups and to help tune the grafting density along with helping to prevent aggregation of the nanoparticles.

In addition to silanes, phosphates or their esters, phosphonates or their esters, and carboxylic acids can be used to bind to the nanoparticles surface. For example, a phosphorus linkage can be utilized between the surface of the nanoparticle and the RAFT agent, such as described in International Patent Publication No. WO 2013078309 (Serial No. PCT/US2012/066254) of Benicewicz, et al., titled "Silicone based nanocomposites including inorganic nanoparticles and their methods of manufacture and use," which is incorporated by reference herein.

Then, to prepare PVP grafted nanoparticles, a RAFT agent according to Formula 1a or 1b above is employed for the polymerization of NVP monomers. As shown in the second reaction step of FIG. 2 in the exemplary reaction schematic, the activated CDPC RAFT agent of formula 3a is attached to the surface of the nanoparticle through the anchoring compound. To attach the RAFT agent onto the anchoring compound of the nanoparticle, the activated CDPC RAFT agent is immobilized onto the surface of the nanoparticle via a condensation reaction with the amine groups of the shown anchoring compound on the nanoparticle's surface. Using this approach, various CDPC-functionalized nanoparticles can be synthesized having a grafting density varying from 0.01-0.7 anchoring compounds/nm$^2$.

Next, two methods can be utilized to form the PVP polymer chain extending from the nanoparticles via the anchoring compound: a "grafting-from" approach and a "grafting-to" approach.

In "grafting-from" embodiments, the PVP polymer chain can be formed by polymerizing a plurality of monomers on the anchored RAFT agent attached to the anchoring compound on the surface of the nanoparticle, with the plurality of monomers comprising the NVP monomer (or a derivative thereof) described above. This polymerization results in the PVP polymer chain being covalently bonded to the surface of the nanoparticle via the anchoring compound. The NVP monomers can be polymerized either alone (i.e., substantially free from any other types of monomers) or in combination with a co-monomer.

Thus, the "grafting-from" method involves formation of the PVP polymer chain onto the anchoring compound and results in the PVP polymeric chain being covalently bonded to the nanoparticle via the anchoring compound (and, if present, a first functionalization compound).

Alternatively, in "grafting to" embodiments, the PVP polymeric chain can be first polymerized and subsequently covalently bonded to the surface of the nanoparticle, either directly or via an anchoring compound (and, if present, a functionalization compound). Thus, in this embodiment, the polymeric chain has been polymerized prior to attachment to the anchoring compound. For example, when polymerized utilizing a RAFT agent, then a reactive end group of the PVP polymer chain (i.e., the RAFT agent group) can react/attach to the anchoring compound.

No matter the method used to attach the polymeric chain to anchoring compound on the nanoparticle, upon attachment, the polymeric chain is, in one particular embodiment, deactivated to prevent further polymerization thereon.

For example, if the "grafting-from" method was utilized to attach the polymeric chain to the anchoring compound via polymerization through a CRP technique (e.g., RAFT), a deactivation agent can be attached to, or reacted with, the end of each polymeric chain to inhibit further polymerization thereon. The deactivation agents can be selected based upon the type of polymerization and/or the type(s) of monomers utilized and can generally include, but are not limited to, amines, peroxides, or mixtures thereof.

On the other hand, if the "grafting-to" method was utilized to attach the polymeric chain to the anchoring compound via attaching a pre-formed polymeric chain, the polymeric chain can be deactivated after or before covalently bonding the polymeric chain to the anchoring compound. Alternatively, the polymeric chain can be deactivated prior to covalently bonding the polymeric chain to the anchoring compound.

The deactivation of the polymeric chain can be achieved by any suitable process. In one embodiment, the polymer chain can be cleaved. Alternatively, the end of the polymer chain can be deactivated. For example, when formed via RAFT polymerization, the types of reactions that can be used to convert RAFT agents to deactivated end groups include reactions with diazo compounds, reactions with nucleophilic reagents such as primary amines, and reactions with oxidation agents which cleave the RAFT agent off the chain end and form an oxidized sulfur group such as sulfonic acid.

C. Bi-Modal Nanoparticles

In addition to PVP, other groups/polymeric chains can be grafted to the surface of the nanoparticles to form a bi-modal nanoparticle. For example, polymeric chains can be grafted to the surface of the nanoparticles, as set forth in U.S. Patent Publication No. 2013/0041112 of Benicewicz, et al., titled "Nanoparticles with Multiple Attached Polymer Assemblies and Use Thereof in Polymer Composites," which is incorporated by reference herein.

Methods to attach such polymeric chains can vary depending on the particular functionality of the chain. See e.g., International Patent Publication No. WO 2013078309 (Serial No. PCT/US2012/066254) of Benicewicz, et al., titled "Silicone based nanocomposites including inorganic nanoparticles and their methods of manufacture and use;" U.S. Provisional Patent Application Ser. No. 61/927,520 of Benicewicz, et al., titled "Butadiene-Derived Polymers Grafted Nanoparticles and Their Methods of Manufacture and Use," filed on Jan. 15, 2014; U.S. Provisional Patent Application Ser. No. 61/946,956 of Benicewicz, et al., titled "Poly Alkyl (Meth)Acrylates Grafted Nanoparticles and Their Methods of Manufacture and Use," filed on Mar. 3, 2013; which are all incorporated by reference herein.

IV. PVP-Grafted Nanoparticles as Drug Delivery Vehicles

The growing phenomenon of bacterial resistance to antibiotics results in high morbidity and mortality, which is an exceptionally urgent healthcare problem. A wide range of antibiotics, such as penicillin, have become ineffective or have limited effectiveness against bacteria since their first usages decades ago. MRSA (methicillin-resistant *Staphylococcus aureus*) is a well-known *bacterium* exhibiting resistance to antibiotics with beta lactam structures, such as penicillin. The resistance makes MRSA-caused infections much more difficult to overcome and, thus, results in an extremely dangerous morbidity. Nanoparticles with a series of advantages, such as high surface to volume ratio and unique nano-size effects, have been employed as drug delivery vehicles. They have been widely used to carry and release active biomolecules to eukaryote cells; however, few groups have applied them to target bacteria, especially MRSA.

In one embodiment, PVP grafted nanoparticles with controlled chain length and graft densities are generally provided for overcoming MRSA infections by conjugating to bacterial resistant antibiotic agent (e.g., penicillin). In particular, the PVP grafted nanoparticles can non-covalently attach to (e.g., via ionic bonding, hydrogen bonding, van der Waals forces, etc.) the antibiotic agent.

EXAMPLE 1

As discussed above, the structure of CPDC contains a pyrrole-based Z group and a tertiary cyanopentanoic R group, which has been demonstrated as a good leaving group in the literature. The strategy for synthesis of RAFT agent CPDC is shown in FIG. 1. Pyrrole was allowed to react with sodium hydroxide in DMSO, followed by addition of carbon disulfide to generate sodium N-pyrroledithiocarboxylate. An excess of potassium ferricyanide was added to oxidize sodium N-pyrroledithiocarboxylate resulting in 1H-pyrrole-1-carbothioic dithioperoxyanhydride, which was further allowed to react with 4,4'-azobis(4-cyanopentanoic acid) to form CPDC. 1H NMR spectra confirmed the peaks at 6.4 ppm and 7.8 ppm assigned to the protons in the pyrrole rings of the intermediate 1H-pyrrole-1-carbothioic dithioperoxyanhydride. The CPDC has a color of pale yellow with a UV-vis strong absorption peaks at 308 nm and 288 nm. Mass spectrum confirmed the molecular weight of CPDC of 268 g/mol. 1H NMR spectra demonstrated the peaks at 1.9 ppm, 2.4 ppm, 2.6 ppm, 6.4 ppm and 7.8 ppm ascribed to the protons in CPDC. The IR spectra demonstrated the presence of the of the peaks at ~1700 cm-1 ascribed to the carbonyl moiety in —COOH, the broad peak at 3400~2400 cm-1 due to the hydroxyl moiety in —COOH, and a range of strong absorption peaks at 1500~600 cm-1 assigned to the pyrrole moiety. Activated CPDC was prepared by the coupling reaction between CPDC and 2-mercaptothiazoline for further use.

The method for synthesis of PVP grafted nanoparticles is shown in FIG. 2. The CPDC anchored silica nanoparticles were prepared by the reaction between amino immobilized nanoparticles with accurately measured densities and activated CPDC. The amount of CPDC coated on nanoparticles can be controlled by changing the feed ratio between amino coated particles and CPDC. The graft density of CPDC was measured precisely by comparing the absorbance of the CPDC coated particles to a UV-vis absorption standard curve (absorbance vs. concentration) of CPDC. The as-synthesized CPDC modified particles possessed a graft density of 0.24 groups/nm$^2$.

The surface-initiated RAFT polymerization of N-Vinylpyrrolidone was operated using a recipe of [NVP]:[CPDC]:[AIBN]=1438:1:0.18 at 80° C. in a mixture solvent of dioxane and anisole. The process of nanoparticle precipitation, centrifugation and redispersion was used to separate any free or unattached chains form the polymer covalently grafted particles. The 1H NMR spectra demonstrated the proton peaks at 1.3-1.8 ppm and 3.5-4.0 ppm ascribed to the attached polymer backbone. The IR spectra of the PVP grafted nanoparticles demonstrated the appearance of the absorption peak at ~2955 cm$^{-1}$, 1655 cm$^{-1}$, 1423 cm$^{-1}$, 1287 cm$^{-1}$, 1065 cm$^{-1}$ due to the methyl group, amide in lactam, —CH$_2$— in lactam, C—N in lactam, and SiO$_2$ moieties respectively. The molecular weight (Mn) of the surface anchored PVP chains was 52500 g/mol and the PDI was 1.31. The thermogravimetric analysis (TGA) confirmed that the anchored PVP chains accounted for 48% by weight. The PVP grafted silica nanoparticle solution was transparent in dimethylsulfoxide (DMSO). The TEM image shows the PVP grafted silica nanoparticles were perfectly dispersed and demonstrates that the size of the nanoparticles was around 20-30 nm (diameter).

EXAMPLE 2

The PVP grafted nanoparticles were employed to non-covalently attach the antibiotic penicillin-G (PenG) and tested for activity against bacteria. Methicillin-resistant Staphylococcus aureus (MRSA)-252, HA-MRSA, CA-MRSA and methicillin-sensitive Staphylococcus aureus (MSSA) were selected as the target bacteria. A control group of free PenG with the same dose was used for the disk diffusion assay of PenG-nanoparticle complex. In addition, PVP grafted silica nanoparticles were tested and exhibited no activity to the four bacteria. The activity tests showed that the PenG-nanoparticle complex exhibited much higher inhibition zones than the free PenG at the same dose by around 14% to 41% (FIGS. 6a-6d). The differences in activities between the two were even significant at low doses against MRSA 252 when the free penicillin-G was completely ineffective. Without wishing to be bound by any particular theory, it is believed that the enhanced inhibition activity was due to the locally high concentrations of antibiotics physically attached to PVP grafted nanoparticles, which overwhelms the bacterial resistance. The small size PVP grafted nanoparticles with controllable surface attached polymer chain lengths offers a significant vehicle to restore antibiotics activities.

In conclusion, a new dithiocarbamate based RAFT agent CPDC for mediating RAFT polymerization of NVP was designed and synthesized. CPDC can also mediate the polymerization of styrene and methyl acrylate in a controlled manner. CPDC was coated on silica nanoparticles via surface silane coupling chemistry. The surface-initiated RAFT polymerization of NVP was conducted on 15 nm (diameter) silica nanoparticles resulting in well-dispersed particles. The synthesis of PVP grafted silica nanoparticles was confirmed by FTIR, TGA, 1H NMR analysis and TEM. The activity of an antibiotic (Penicillin-G) over bacteria methicillin-resistant Staphylococcus aureus (MRSA) was significantly increased when physically bound to the PVP grafted silica nanoparticles. PVP grafted silica nanoparticles appear to be a new vehicle to efficiently restore antibiotic activity.

Experimental Section for Examples 1 and 2

Materials: All chemicals were obtained from Fisher or Acros and used as-received unless otherwise specified. 3-Aminopropyldimethylethoxysilane was obtained from Gelest and used as-received. The amino-functionalized silica nanoparticles were prepared according to the literature. 1 N-vinylpyrrolidone was purified by distillation under reduced pressure before use. The penicillin-G sodium salt was purchased from Sigma-Aldrich Inc. and used as-received. AIBN was recrystallized from methanol before use.

Bacteria Strains: MRSA 252 (ATCCBAA-1720); Staphylococcus aureus ATCC 29213 (community acquired-MRSA); Staphylococcus aureus ATCC BAA 1717 (hospital associated-MRSA); MSSA ATCC BAA 1718. These bacterial strains were grown at 37° C. in tryptic soy broth for 24 hours.

Instrumentation: $^1$H NMR (Varian Mercury spectrometer 300/400) was conducted using CDCl$_3$ or CD$_3$OD as the solvent. Molecular weights and PDI were determined using a gel permeation chromatography (GPC) equipped with a 515 HPLC pump, a 2410 refractive index detector, and three Styragel columns. The columns consisted of HR1, HR3 and HR4 in the effective molecular weight ranges of 100-5000, 500-30000, and 5000-500000, respectively. The GPC used THF as eluent at 30° C. and a flow rate of 1.0 mL/min and was calibrated with poly(methyl methacrylate) or polystyrene standards obtained from Polymer Laboratories. The polymer grafted nanoparticles were cleaved by HF before GPC analysis. Samples were filtered through microfilters with a pore size of 0.2 μm before injection. Infrared spectra were recorded with a PerkinElmer Spectrum 100 spectrometer. UV-vis spectra were measured with a Perkin-Elmer Lambda 4C UV-vis spectrophotometer. TEM images were examined using a Hitachi 8000 transmission electron microscope with an operating voltage of 200 kV. Carbon-coated copper grids were used to prepare samples by dropping sample solutions on the grids followed by drying in a fume hood before use. TGA measurement was conducted using a TA Instruments Q5000 with a heating rate of 10° C./min form 25° C. to 950° C. under nitrogen flow. Differential scanning calorimetry (DSC) measurement was conducted using a TA Instruments Q2000 under nitrogen flow.

Synthesis of 4-Cyanopentanoic Acid N-pyrroledithiocarboxylate (CPDC)

Pyrrole (2.68 g, 0.04 mol) was added dropwise to a DMSO solution (30 mL) of sodium hydroxide (0.96 g, 0.04 mol) at room temperature. The resulting brown solution then was stirred at room temperature for 30 minutes. After that, carbon disulfide (3.04 g, 0.04 mol) was added to the solution followed by another 30 minutes stirring. Excess amount of aqueous solution of potassium ferricyanide (14.48 g) was added dropwise to the solution and the resulting mixture was stirred for 30 min. The product was formed and further washed by DI water until the washings were colorless. The product was dried overnight under vacuum and obtained as a coffee color solid (yield: 61%, 3.46 g). $^1$H NMR (300 MHz, CDCl$_3$): δ (ppm) 6.45 (m, 4H, =CHN), 7.77 (m, 4H, =CH).

1H-pyrrole-1-carbothioic dithioperoxyanhydride (1.10 g, 3.87 mmol) and 4,4'-azobis(4-cyanopentanoic acid) (1.69 g, 6.029 mmol) were dissolved in 70 mL ethyl acetate. The reaction solution was heated at 75° C. for 18 hours. Then the solvent was removed and the crude product was passed through silica gel column chromatography (hexane:ethyl acetate=3:2). The product was obtained as a pale yellow solid (yield: 2.08 g, 88.3%). $^1$H NMR (300 MHz, CD$_3$OD): δ (ppm) 1.97 (s, 3H, C(CH$_3$)CN), 2.39-2.58 (m, 2H, C(CN)CH$_2$), 2.66 (t, 2H, CH$_2$—C(=O)—O), 6.42 (m, 2H, =CHN), 7.70 (m, 2H, =CH). $^{13}$C NMR (300 MHz, CD$_3$OD): δ (ppm) 23.46 (CH$_3$), 29.05 (CH$_2$—C(=O)), 33.36 (C(CN)CH$_2$), 46.33 (C(CH$_3$)CN), 114.60 (=CH), 118.59 (C(CH$_3$)CN), 120.18 (=CHN), 173.65 (C(=O)O), 193.28 (C=S). Melting point: 114° C. Mass spectroscopy: m/z: 268 (theoretical m/z: 268).

Activation of CPDC: 4-Cyanopentanoic acid N-pyrroledithiocarboxylate (0.285 g, 1.064 mmol) and 2-mercaptothiazoline (0.127 g, 1.064 mmol), and dicyclohexylcarbodiimide (DCC) (0.264 g, 1.277 mmol) were dissolved in 20 mL of dichloromethane. (Dimethylamino)pyridine (DMAP) (13.0 mg, 0.11 mmol) was subsequently added. The resulting solution was stirred at room temperature for 6 hours. After removal of the solvent, the crude product was passed through silica gel column chromatography (hexane:ethyl acetate=5:4). The product was obtained with a dark yellow color (yield: 0.246 g, 62.5%). $^1$HNMR (300 MHz, CDCl$_3$): δ (ppm) 1.91 (s, 3H, C(CH$_3$)CN), 2.60 (m, 2H, C(CN)CH$_2$), 3.26 (t, 2H, —CH$_2$SC(=S)), 3.66 (t, 2H, —CH$_2$C(=O)N), 4.52 (t, 2H, —C(=O)NCH$_2$), 6.30 (m, 2H, =CHN), 7.54 (m, 2H, =CH).

Synthesis of CPDC Functionalized SiO$_2$ Nanoparticles: A THF stock solution (4.10 mL) of activated CPDC (0.05 mol/L) was diluted in 20 mL dry THF. A THF solution of amino-functionalized silica nanoparticles (approx. 3 g) was added slowly to the above activated CPDC solution and the resulting mixture was stirred at room temperature for 6 hours. After the reaction, the solution was precipitated into cyclohexane and ethyl ether mixture. (300 mL, cyclohexane:ethyl ether=4:1), centrifuged at 3000 rpm for 5 minutes, and re-dispersed in dry THF. This procedure was repeated several times until the supernatant solution was colorless after centrifugation. The light yellow CPDC anchored nanoparticles were dried under vacuum at room temperature.

Surface-Initiated RAFT Polymerization of NVP from CPDC Anchored SiO$_2$ Nanoparticles: NVP (0.44 mL, 4.114×10$^{-3}$ mol), CPDC coated SiO$_2$ nanoparticles (50.26 mg), dry dioxane (1.5 mL) and anisole (1.5 mL) were added to a 20 mL Schlenk tube. After sonication for 1 minute, AIBN (51 μL, 10 mM in dioxane) was added. The solution was degassed by four freeze-pump-thaw cycles, filled with nitrogen, and then placed in an oil bath at 80° C. for various intervals. The polymerization was stopped by quenching in ice water. The grafted PVP was then cleaved.

Preparation of Nanoparticle-PenG Complex: To prepare the nanoparticle-PenG complex, 15 μL of PVP grafted silica nanoparticles solution (26.65 mg/ml) and 1.85 mL DI water were mixed. 200 μL Penicillin G sodium salt aqueous solution (1 mg/mL) was added and incubated at 24° C. (3 hours) with shaking. The resulting solutions were centrifuged at 10,000 rpm for 6-8 minutes via Amicon centrifuge tubes. The pellet was collected, resuspended, and washed again via the centrifugation. The process was repeated several times, and the nanoparticle-PenG complex was finally collected. According to the UV-vis analysis of the supernatant, the un-conjugated PenG levels in the supernatant were negligible. Thus, it was assumed that majority of the PenG was conjugated to PVP grafted nanoparticles.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of grafting a PVP polymer onto a nanoparticle, the method comprising:
polymerizing a plurality of monomers in the presence of a RAFT agent to form a polymeric chain covalently bonded to the nanoparticle, wherein the plurality of monomers comprises N-vinylpyrrolidone, and wherein the RAFT agent is selected from the group consisting of:

where $R_1$ is H or a $C_1$ to $C_5$ alkyl group; $R_2$ is an electron withdrawing group; $R_3$ is a hydroxyl group, a thioazoline group, or an ether group; and n is 1 to 12; and where $R_4$ is H or a $C_1$ to $C_5$ alkyl group; $R_6$ is an electron withdrawing group; $R_6$ is a hydroxyl group, a thioazoline group, or an ether group; and m is 1 to 12.

2. The method of claim 1, wherein $R_1$ or $R_4$ is H.

3. The method of claim 1, wherein $R_2$ or $R_5$ is CN, NO$_2$, SO$_3$H, or a halogen.

4. The method of claim 3, wherein $R_2$ or $R_5$ is a nitrile group.

5. The method of claim 1, wherein n or m is 2.

6. The method of claim 1, wherein $R_3$ or $R_6$ is $OR_7$ with $R_7$ being a $C_1$ to $C_5$ alkyl group.

7. The method of claim 1, wherein $R_3$ or $R_6$ is a hydroxyl group.

8. The method of claim 1, wherein $R_3$ or $R_6$ is a thioazoline group.

* * * * *